United States Patent
Nishimura et al.

(10) Patent No.: US 10,088,402 B2
(45) Date of Patent: Oct. 2, 2018

(54) THERMO-GRAVIMETRIC APPARATUS

(71) Applicant: Hitachi High-Tech Science Corporation, Minato-ku, Tokyo (JP)

(72) Inventors: Shinya Nishimura, Tokyo (JP); Kentaro Yamada, Tokyo (JP); Kanji Nagasawa, Tokyo (JP); Ryoji Takasawa, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 445 days.

(21) Appl. No.: 14/560,003

(22) Filed: Dec. 4, 2014

(65) Prior Publication Data

US 2015/0153292 A1    Jun. 4, 2015

(30) Foreign Application Priority Data

Dec. 4, 2013    (JP) .................................. 2013-251101

(51) Int. Cl.
   *G01N 5/04*    (2006.01)
   *G01N 25/00*   (2006.01)
   *G01N 5/00*    (2006.01)

(52) U.S. Cl.
   CPC ...................... *G01N 5/00* (2013.01)

(58) Field of Classification Search
   CPC ........ G01N 25/00; G01N 25/20; G01N 17/00; G01N 25/02; G01N 5/04; G01N 1/44; G01N 33/00; G01N 25/482; G01N 25/486
   USPC ........ 374/10, 11, 12, 13, 14, 30–39; 422/51; 436/147
   See application file for complete search history.

(56) References Cited

U.S. PATENT DOCUMENTS 3,373,598 A * 3/1968 Johnson ................... G01G 1/00
                                                    374/14
3,469,455 A * 9/1969 Iwata ....................... G01G 1/00
                                                    177/253

(Continued)

FOREIGN PATENT DOCUMENTS

JP    S59-142696 U    9/1984
JP    H07-146262 A    6/1995

(Continued)

OTHER PUBLICATIONS

Sep. 20, 2016—(JP) Notification of Reasons for Refusal—App 2013-251101.

*Primary Examiner* — Gail Kaplan Verbitsky
(74) *Attorney, Agent, or Firm* — Banner & Witcoff, Ltd.

(57) ABSTRACT

A thermal analyzer is provided with: a furnace tube; a pair of sample holders; a heating furnace; a measurement chamber; and a measurement unit arranged inside the measurement chamber. The sample holders are arranged inside the furnace tube and are provided with mounting faces on which a pair of sample containers are mounted respectively. The heating furnace has an opening through which a measurement sample is observable, the opening being located at a position above the center of a virtual segment which connects centers of gravity of the mounting faces of the sample holders. The opening is formed to have a size, as viewed in a direction perpendicular to the axial direction and the mounting faces, of 7 mm or more in the direction along the virtual segment and of 3 mm or more in the direction perpendicular to the virtual segment.

7 Claims, 9 Drawing Sheets

(56) References Cited

U.S. PATENT DOCUMENTS

| | | | | |
|---|---|---|---|---|
| 5,601,364 A * | 2/1997 | Ume | | G01B 11/167 |
| | | | | 250/237 G |
| 5,669,554 A * | 9/1997 | Nakamura | | B01F 3/022 |
| | | | | 165/222 |
| 5,876,118 A * | 3/1999 | Vogel | | G01N 25/4826 |
| | | | | 374/11 |
| 6,210,035 B1 * | 4/2001 | Nakamura | | G01N 25/4813 |
| | | | | 374/10 |
| 6,257,757 B1 | 7/2001 | Nakamura | | |
| 7,500,779 B2 * | 3/2009 | Takeuchi | | G01N 5/04 |
| | | | | 374/10 |
| 8,359,180 B2 * | 1/2013 | Yamada | | G01K 17/00 |
| | | | | 374/127 |
| 9,033,574 B2 * | 5/2015 | Nagasawa | | G01N 25/00 |
| | | | | 374/10 |
| 9,691,594 B2 * | 6/2017 | Arii | | G01N 25/20 |
| 9,816,907 B2 * | 11/2017 | Schawe | | G01N 5/04 |
| 9,885,645 B2 * | 2/2018 | Nishimura | | G01N 5/04 |
| 2004/0048385 A1 * | 3/2004 | Brent | | G01N 19/04 |
| | | | | 436/55 |
| 2007/0201533 A1 * | 8/2007 | Takeuchi | | G01N 5/04 |
| | | | | 374/14 |
| 2011/0054829 A1 | 3/2011 | Yamada | | |
| 2013/0235899 A1 | 9/2013 | Nagasawa et al. | | |
| 2015/0264277 A1 * | 9/2015 | Nishimura | | H04N 5/2252 |
| | | | | 348/164 |

FOREIGN PATENT DOCUMENTS

| | | |
|---|---|---|
| JP | H08-327573 A | 12/1996 |
| JP | H11-326249 A | 11/1999 |
| JP | 2001-183319 A | 7/2001 |
| JP | 2007-232479 A | 9/2007 |
| JP | 2011-053077 A | 3/2011 |
| JP | 2013-185834 A | 9/2013 |

\* cited by examiner (a) WITH OPENING W (PRESENT INVENTION)
(b) WITHOUT OPENING W (COMPARATIVE EXAMPLE)

THERMO-GRAVIMETRIC APPARATUS

CROSS-REFERENCE TO RELATED APPLICATION

This application claims priority from Japanese Patent Application No. 2013-251101, filed on Dec. 4, 2013, the entire subject matter of which is incorporated herein by reference.

BACKGROUND

1. Technical Field

The present invention relates to a thermal analyzer for measuring a physical change of a sample along with its temperature change caused by heating the sample.

2. Description of the Related Art

Conventionally, as a technique of evaluating temperature characteristics of a sample, there has been employed a technique called thermal analysis for measuring a physical change of a sample along with its temperature change caused by heating the sample. A definition of thermal analysis can be found in JIS K 0129: 2005 "General rules for thermal analysis," and thermal analysis, according to this definition, includes all techniques that measure the physical properties of a measurement target (sample) under program controlled temperatures. Five common thermal analysis methods are (1) Differential Thermal Analysis (DTA) that detects temperatures (temperature difference), (2) Differential Scanning Calorimetry (DSC) that detects a heat flow difference, (3) Thermogravimetry (TG) that detects masses (weight change), (4) Thermomechanical Analysis (TMA) and (5) Dynamic Mechanical Analysis (DMA) that detect mechanical properties.

The thermal analyzer 1000 shown in FIG. 9 represents a known example of thermal analyzers. The thermal analyzer 1000 performs Thermogravimetry (TG), and, as required, Differential Thermal Analysis (DTA). This thermal analyzer is provided with: a cylindrical furnace tube 9 having an outlet 9b which is reduced in diameter and is arranged at an anterior end portion 9a; a cylindrical heating furnace 3 surrounding the furnace tube 9 from outside; sample holders 41 and 42 arranged inside the furnace tube 9 and holding samples $S_1$ and $S_2$, respectively, via sample containers; a measurement chamber 30 connected air tight to a posterior end portion 9d of the furnace tube 9; and a weight detector 32 arranged inside a measurement chamber 30 to measure weight changes of samples (cf. JP-A-11-326249, JP-A-2007-232479, and JP-A-7-146262). The thermal analyzer also includes two supporting pillars 218 extending downward from the lower end of the heating furnace 3. The supporting pillars 218 are connected to a support base 200. A flange 7 is fixed to the outer side of the posterior end portion 9d of the furnace tube 9, and a supporting pillar 216 extends downward from the lower end of the flange 7. The supporting pillar 216 is also connected to the support base 200. The support base 200 and the measurement chamber 30 are mounted on a base 10. The support base 200 can be moved back and forth with a linear actuator 220 along the axial direction O of the furnace tube 9.

The heating furnace 3 heats the sample holders 41 and 42 from outside of the furnace tube 9, and the weight detector 32 detects the weights of the samples $S_1$ and $S_2$ as they change with temperature.

Referring to FIG. 10, the linear actuator 220 moves the support base 200 toward the anterior side of the furnace tube 9 (leftward in FIG. 10) when setting samples $S_1$ and $S_2$ to the sample holders 41 and 42 or when replacing samples $S_1$ and $S_2$, together with the heating furnace 3 and the furnace tube 9 fixed to the support base 200. This exposes the sample holders 41 and 42 on the posterior side of the furnace tube 9, enabling setting or replacing the samples $S_1$ and $S_2$.

While the foregoing thermal analyzer can be used to detect the required thermophysical properties, changes in the sample being studied by thermal analysis cannot be visually observed. This is because the furnace tube 9 is typically formed of a ceramic such as sintered alumina, or a heat resistant metal such as Inconel (registered trademark), and is covered with the heating furnace 3.

With respect to these conventional thermal analyzers, the Applicants of the present application have proposed, in JP-A-2013-185834, a new thermal analyzer that includes a furnace tube formed of a transparent material, and in which the furnace tube is exposed by moving forward only the heating furnace for sample observation so that a sample can be observed from outside of the exposed furnace tube. It is also proposed in JP-A-2013-185834 to cover a part of the exposed furnace tube with a heat conducting member, and partially inserting the heat conducting member into the heating furnace to transfer the heat of the heating furnace to the exposed furnace tube, and maintain the sample in a heated state at the sample observation position.

A thermal analysis using the technique in JP-A-2013-185834 enables a sample observation at temperatures as high as 500° C. when the technique is adapted to indirectly heat the sample inside the exposed furnace tube with the heat conducting member. However, such indirect heating with the heat conducting member may not be sufficient to meet the requirement for observing a sample at high temperatures above 500° C. in a thermal analysis.

When performing the Thermogravimetry/Differential Thermal Analysis (TG/DTA) as shown in FIG. 9, the measurement sample $S_1$ is covered with the heating furnace 3. For this reason, as shown in FIG. 6, the radiation heat RH from the heating furnace 3 directly radiates onto the measurement sample $S_1$ inside the sample container 51. DTA obtains a differential heat signal resulting from the melting, decomposition, or other changes of the measurement sample $S_1$. However, the amount of the radiation heat RH absorbed by the measurement sample $S_1$ changes when changes occur in sample color, or when the measurement sample $S_1$ melts and changes its shape under heat. Such changes in radiation heat are reflected in the differential heat signal, and the measurement accuracy suffers.

SUMMARY

The present invention has been made in view of the above-described circumstances, and one of objects of the present invention is to provide a thermal analyzer that can be used to observe a sample with a furnace tube as changes occur in the sample in a thermal analysis, and with which the measurement accuracy of thermal analysis can be improved through the reduction of the radiation heat that directly radiates from a heating furnace onto the sample inside the furnace tube.

In order to solve the above-mentioned problem, according to an exemplary embodiment of the present invention, there is provided a thermal analyzer including: a furnace tube made of a transparent material in a cylindrical shape, the furnace tube having an outlet at an anterior end portion thereof in an axial direction; a pair of sample holders arranged inside the furnace tube and each comprising a mounting face on which a pair of sample containers each containing a measurement sample and a reference sample are mounted respectively; a heating furnace configured to have a cylindrical shape and to surround the furnace tube from outside; a measurement chamber connected air-tight to the furnace tube at a posterior end portion of the furnace tube in the axial direction; and a measurement unit arranged inside the measurement chamber and measures changes in the physical properties of the measurement sample and the reference sample. The heating furnace includes an opening through which the measurement sample is observable, the opening being located at a position above the center of a virtual segment which connects centers of gravity of the mounting faces of the sample holders. The opening is formed to have a size, as viewed in a direction perpendicular to the axial direction and the mounting faces, of 7 mm or more in the direction along the virtual segment and of 3 mm or more in the direction perpendicular to the virtual segment.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

An embodiment of the present invention is described below with reference to the accompanying drawings. In the following, the term "anterior end (side)" will be used to refer to the anterior end portion 9a side of a furnace tube 9 in a direction along axial direction O, and the term "posterior end (side)" will be used to refer to the opposite side of the furnace tube 9.

Figure 1:
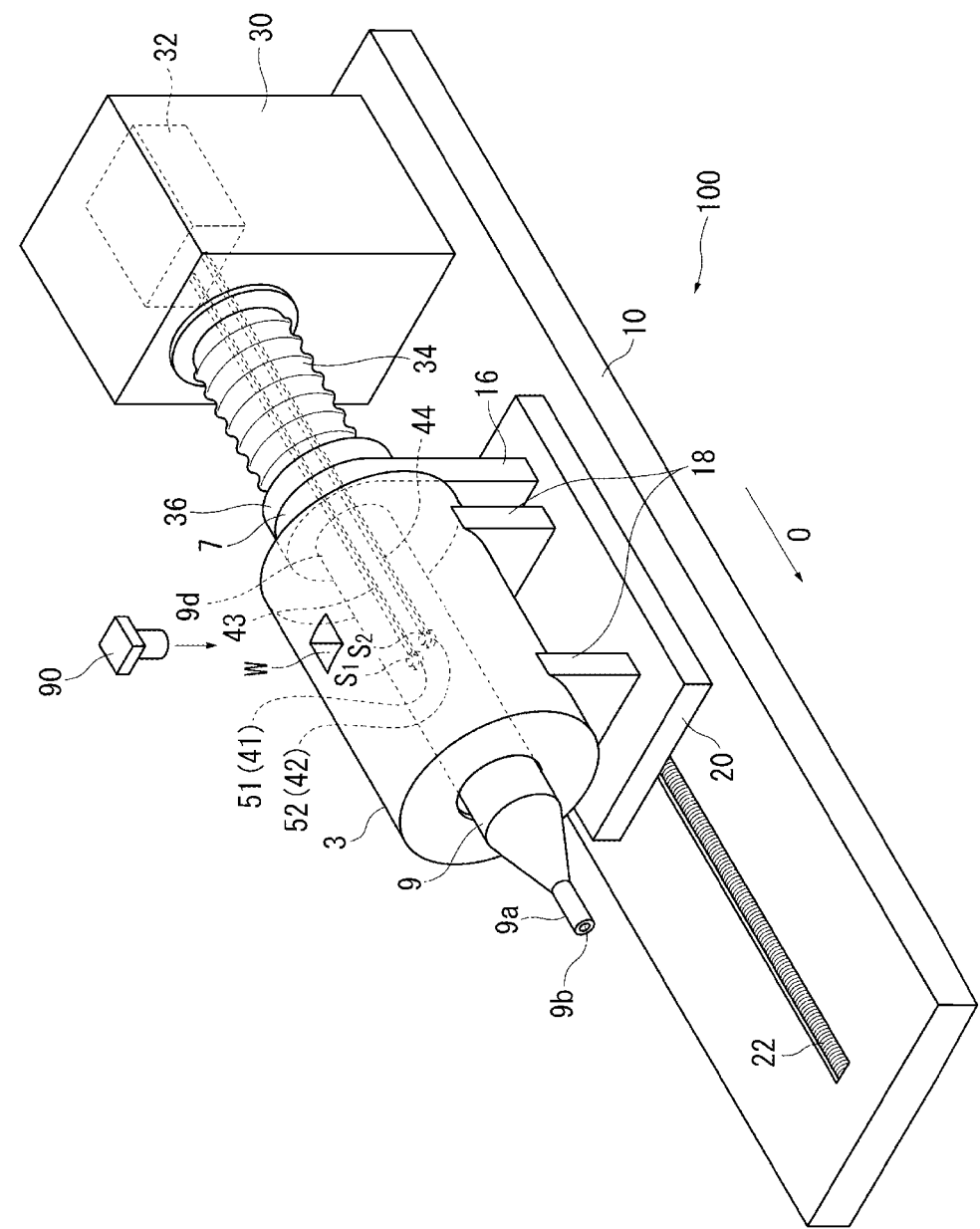
FIG. 1 is a perspective view illustrating a configuration of the thermal analyzer according to an embodiment of the present invention.
Figure 2:
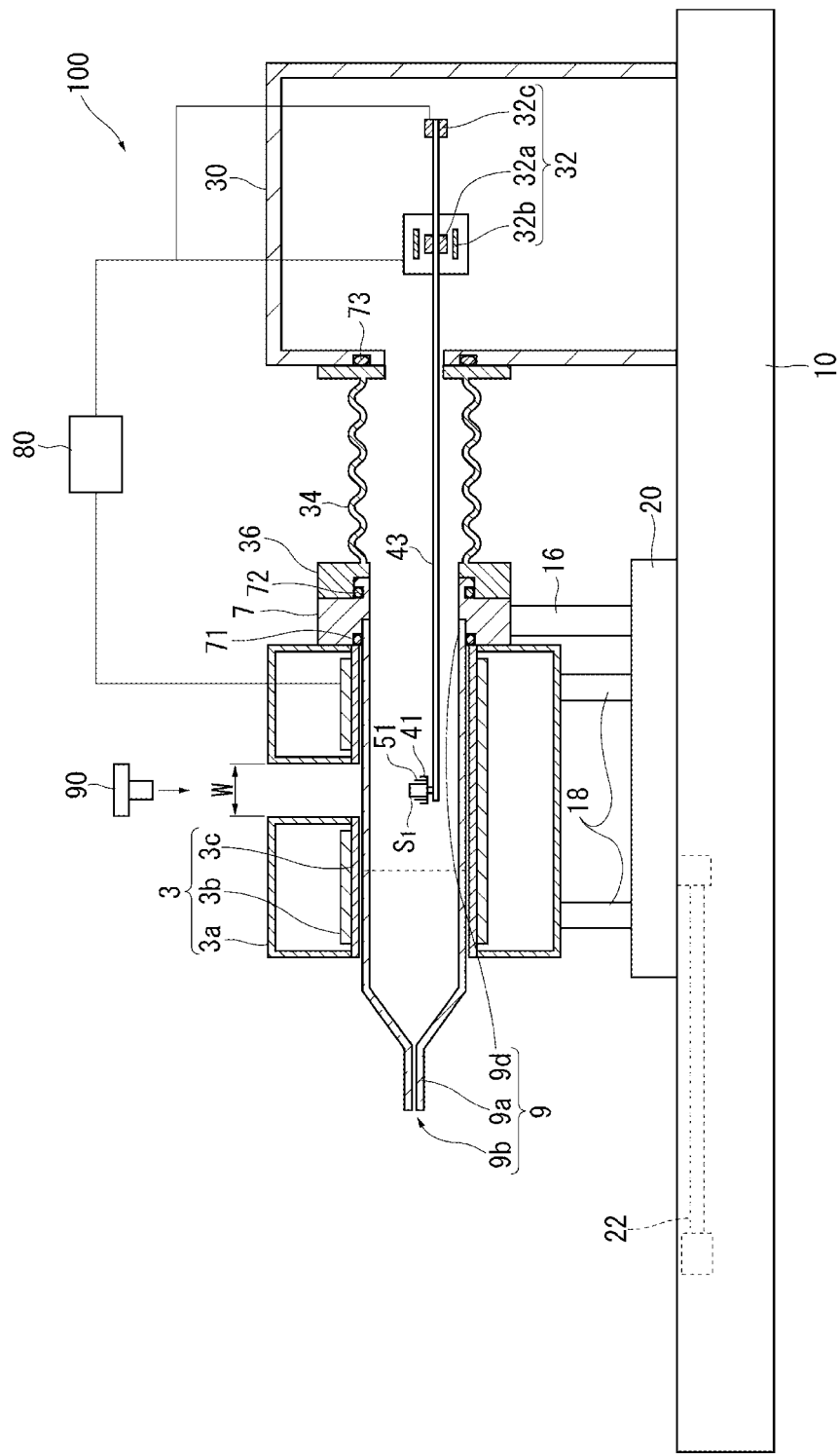
FIG. 2 is a cross sectional view of the thermal analyzer taken in a vertical section that passes an axis of a furnace tube.

FIG. 1 is a perspective view of a configuration of a thermal analyzer 100 according to the embodiment of the present invention. FIG. 2 is a cross sectional view of the thermal analyzer 100 taken in a vertical section that passes an axis of the furnace tube 9.

The thermal analyzer 100 is configured as a Thermogravimetric (TG) apparatus, and is provided with: a cylindrical furnace tube 9; a cylindrical heating furnace 3 surrounding the furnace tube 9 from outside; a pair of sample holders 41 and 42 arranged inside the furnace tube 9; a support base 20; a measurement chamber 30 connected to a posterior end portion 9d of the furnace tube 9; a weight detector 32 arranged inside the measurement chamber 30 to measure the weight changes of samples $S_1$ and $S_2$ (corresponds to "measurement unit" of the claims); and a base 10 with the measurement chamber 30 mounted on the top face. A measurement sample (sample) $S_1$ and a reference sample $S_2$ are housed in a pair of sample containers (see FIG. 2) 51 and 52, respectively. The sample containers 51 and 52 are mounted on the sample holders 41 and 42, respectively. The reference sample $S_2$ is a reference material (reference) for the measurement sample.

Two supporting pillars 18 extend downward from the lower end portions near the both ends of the heating furnace 3 in the axial direction, and are connected to the top face of the support base 20. A flange 7 is fixed to the outer side of the posterior end portion 9d of the furnace tube 9, and a supporting pillar 16 extends downward from the lower end of the flange 7. The supporting pillar 16 is connected to the top face of the support base 20. The supporting pillar 16 is arranged more toward the posterior side from the posterior end of the support base 20 so as not to interfere with the support base 20. The furnace tube 9 may be fixed to the heating furnace 3, and the supporting pillar 16 may be structurally omitted in this case.

The base 10 has a groove formed along the axial direction O, and a linear actuator 22 is arranged in the groove. The posterior end of the linear actuator 22 is connected to the support base 20, and the anterior end (servomotor) is connected to the base 10. The support base 20 can be moved back and forth with the linear actuator 22 along the groove in the axial direction O.

The linear actuator 22 may be configured from components, for example, such as a ball screw and a servomotor, and may be configured by any known actuator capable of linear actuation along axial direction O.

The heating furnace 3 has a cylindrical furnace core tube 3c forming the inner surface of the heating furnace 3, a heater 3b fitted to the furnace core tube 3c, and a cylindrical outer cylinder 3a having side walls at the both ends (see FIG. 2). A center hole for inserting the furnace core tube 3c is provided at the center of the both side walls of the outer cylinder 3a. The outer cylinder 3a surrounds the heater 3b, and insulates the heating furnace 3. The outer cylinder 3a may be appropriately provided with an adjusting hole (not illustrated) to adjust the temperature of the heating furnace 3. The inner diameter of the furnace core tube 3c is larger than the outer diameter of the furnace tube 9, and the heating furnace 3 heats the furnace tube 9 (and the samples $S_1$ and $S_2$ inside the furnace tube 9) in a non-contact fashion.

At the top face of the heating furnace 3 is formed a substantially rectangular opening W, penetrating through the outer cylinder 3a toward the furnace core tube 3c. The opening W will be described later.

The furnace tube 9 is reduced in diameter to have a tapered shape toward the anterior end portion 9a. The anterior end portion 9a is formed into an elongated capillary shape, and has an outlet 9b at the anterior end. A purge gas is appropriately introduced into the furnace tube 9 from the posterior side. Waste products such as the purge gas, and a heat decomposition product of the sample are discharged through the outlet 9b. A ring-like flange 7 is attached to the posterior end portion 9d of the furnace tube 9 via a sealing member 71 (see FIG. 2).

The furnace tube 9 is made of a transparent material, allowing the samples $S_1$ and $S_2$ to be observed from outside of the furnace tube 9. As used herein, "transparent material" refers to materials that pass visible light at a predetermined optical transmittance, and includes semitransparent materials. Preferred for use as the transparent material are quartz glass, sapphire glass, and YAG (yttrium aluminum garnet) ceramic.

The sample holders 41 and 42 are connected to balance arms 43 and 44, respectively, that extend toward the posterior side along the axial direction O. The balance arms 43 and 44 are horizontally arranged side by side. Thermocouples are installed directly below the sample holders 41 and 42 to allow for sample temperature measurement. The balance arms 43 and 44, and the sample holders 41 and 42 are made of, for example, platinum.

The measurement chamber 30 is arranged at the posterior end of the furnace tube 9, and a tubular bellows 34 extending out to the furnace tube 9 toward the anterior side of the axial direction O is attached to the anterior end portion of the measurement chamber 30 via a sealing member 73. The anterior side of the bellows 34 forms a flange 36. The flange 36 is connected air tight to the flange 7 via a sealing member 72. The measurement chamber 30 and the furnace tube 9 are thus in communication with each other inside, and the posterior end of the balance arms 43 and 44 extends into the measurement chamber 30 from the furnace tube 9. The sealing members 71 to 73 may use, for example, O-rings, or gaskets.

As illustrated in FIG. 2, the weight detector 32 arranged inside the measurement chamber 30 includes a coil 32a, a magnet 32b, and a position detector 32c. The position detector 32c is configured by, for example, a photosensor. The position detector 32c is arranged on the posterior side of each of the balance arms 43 and 44, and detects whether the balance arms 43 and 44 are horizontal. The coil 32a is attached to the axial center (fulcrum) of the balance arms 43 and 44, and the magnet 32b is arranged on the both sides of the coil 32a. A current is passed through the coil 32a to make the balance arms 43 and 44 horizontal, and the current is measured to find the weight of each sample $S_1$ and $S_2$ at the anterior end of the balance arms 43 and 44. The weight detector 32 is provided for each of the balance arms 43 and 44.

As illustrated in FIG. 2, the linear actuator 22, the heater 3b, and the weight detector 32 are controlled by a controller 80 configured by, for example, a computer. Specifically, the controller 80 electrically controls the heater 3b to heat the samples $S_1$ and $S_2$ in the sample containers 51 and 52 with the predetermined patterns of the transferred heat through the furnace tube 9. The differential heat and the temperatures of the samples $S_1$ and $S_2$ are obtained by the thermocouples arranged directly below the sample holders 41 and 42, and the weight detector 32 obtains the weight changes of the samples. The controller 80 controls the operation of the linear actuator 22 to move the heating furnace 3 and the furnace tube 9 to the measurement position and the sample setting position, as described below.

Note that, the "measurement position" refers to a position of the heating furnace 3 and the furnace tube 9 at which the flange 36 and the flange 7 are connected to each other air tight and the heating furnace 3 covers the sample holders 41 and 42 (that is, samples $S_1$ and $S_2$) of the furnace tube 9.

Figure 3:
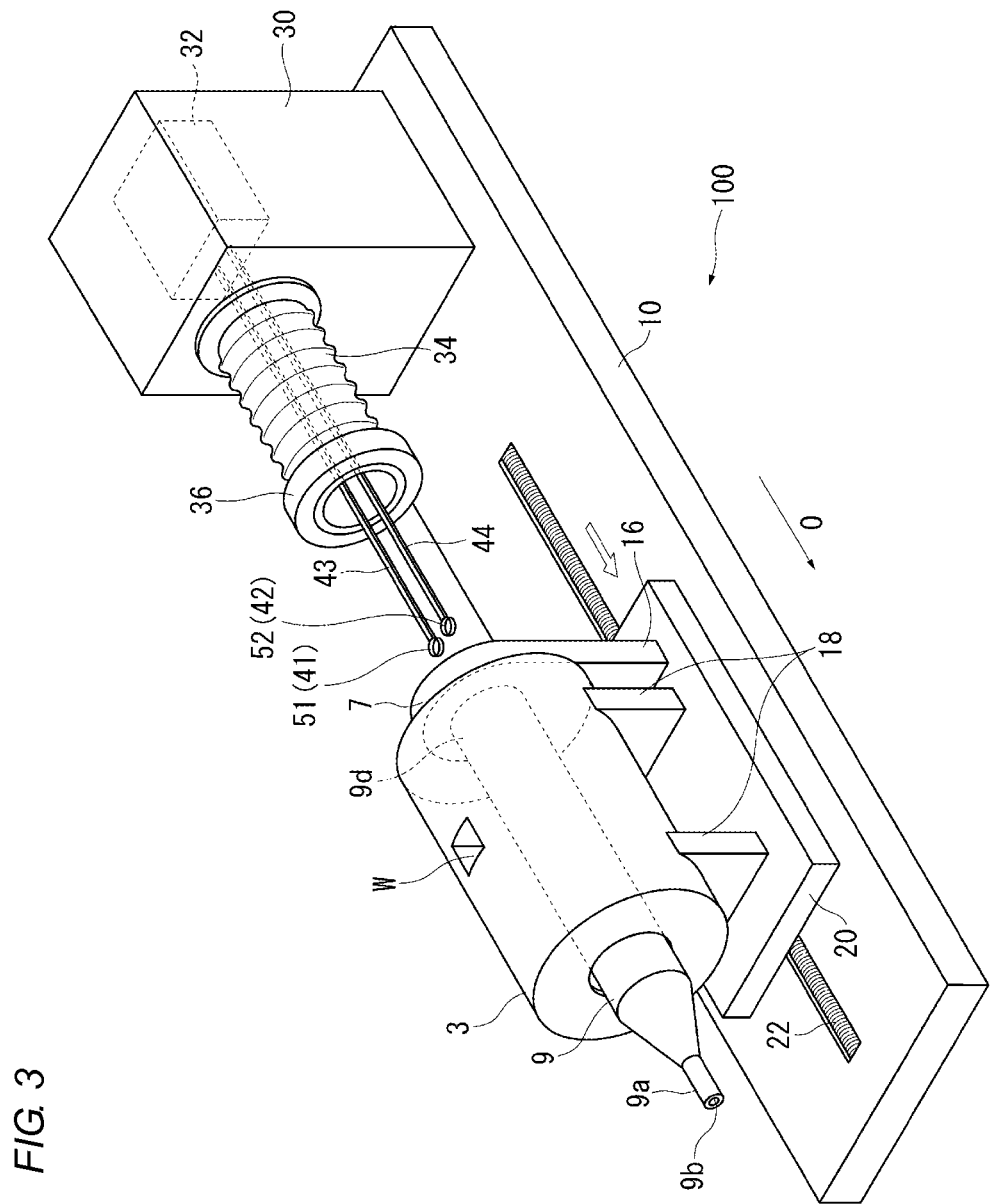
FIG. 3 is a diagram showing how samples are set or replaced in the thermal analyzer.

FIG. 3 illustrates the positions of the heating furnace 3 and the furnace tube 9 when samples $S_1$ and $S_2$ are set in the sample containers 51 and 52 on the sample holders 41 and 42, or when samples $S_1$ and $S_2$ are replaced. When setting (disposing) or replacing samples $S_1$ and $S_2$, the linear actuator 22 moves the support base 20 toward the anterior side of the furnace tube 9 (leftward in FIG. 3). This moves the furnace tube 9 and the heating furnace 3 fixed to the support base 20 toward the anterior side relative to the measurement position, and exposes the sample holders 41 and 42 on the posterior side of the furnace tube 9 and the heating furnace 3, allowing the samples $S_1$ and $S_2$ to be set or replaced.

The "sample setting position" herein refers to a position of the heating furnace 3 and the furnace tube 9 at which, as illustrated in FIG. 3, the flange 36 and the flange 7 are separated from each other in the axial direction O and the sample holders 41 and 42 (that is, samples $S_1$ and $S_2$) are exposed on the rear end side with respect to the furnace tube 9 and the heating furnace 3.

Figure 4:
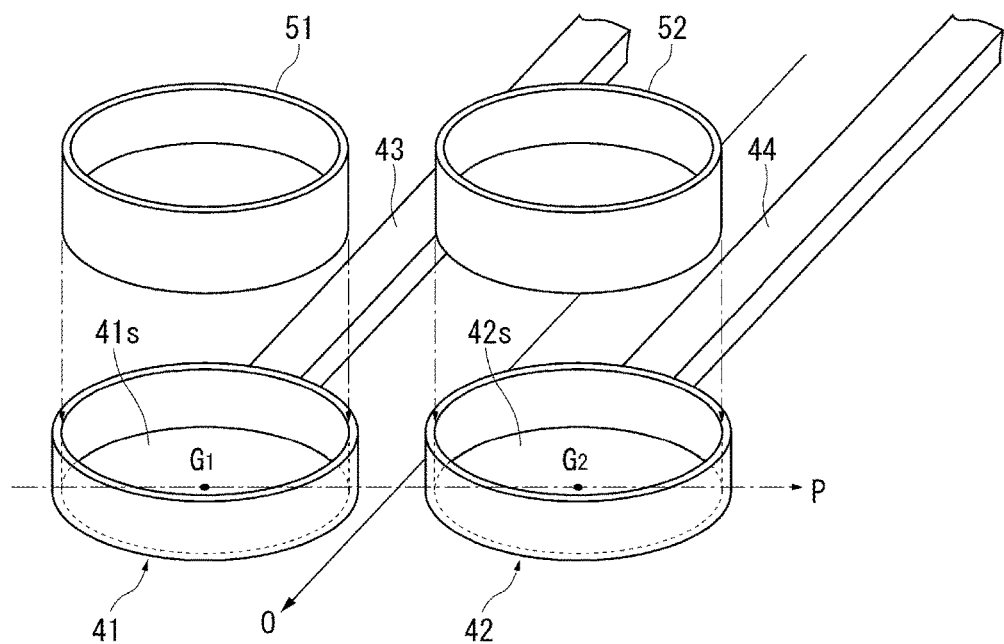
FIG. 4 is a diagram showing how sample containers are mounted on the mounting faces of sample holders.

The opening W is described below with reference to FIGS. 4 to 5. As illustrated in FIG. 4, the sample holders 41 and 42 each have a form of a circular dish, and the bottom faces serve as mounting faces 41s and 42s for mounting the sample containers 51 and 52, respectively. The sample holders 41 and 42 are arranged side by side in a direction perpendicular to axial direction O. The sample holders 41 and 42 are positioned in such a manner that these are axisymmetrical to each other about the axial direction O, and the direction P perpendicular to the axial direction O, and that the samples $S_1$ and $S_2$ held on the sample holders 41 and 42 via the sample containers are heated under the same condition inside the furnace tube 9. The sample containers 51 and 52 are mounted so that their centers of gravity (not illustrated) match the centers of gravity G1 and G2 of the mounting faces 41s and 42s, respectively.

The sample container 51 for holding the measurement sample $S_1$ is an open-top, bottomed cylindrical container with an open top to allow observation of measurement sample $S_1$. On the other hand, the sample container 52 for holding the reference sample $S_2$ does not need to be observable, and may be a closed container, instead of an open-top bottomed container. It is, however, preferable that the sample container 52 has the same shape as the sample container 51 to ensure that the samples $S_1$ and $S_2$ are heated under the same conditions inside the furnace tube 9.

The inner diameter of the sample container 51 is about 3 mm at minimum. It is thus possible to observe the measurement sample $S_1$ through the opening W when the opening W is formed over the inside of the sample container 51. On the other hand, in order to heat the samples $S_1$ and $S_2$ under the same conditions inside the furnace tube 9, the same opening W needs to be provided for the container 51 and the container 52.

For a given size of the sample holders 41 and 42, the observation field of the measurement sample $S_1$ varies with the container inner diameter of the sample container.

Figure 5:
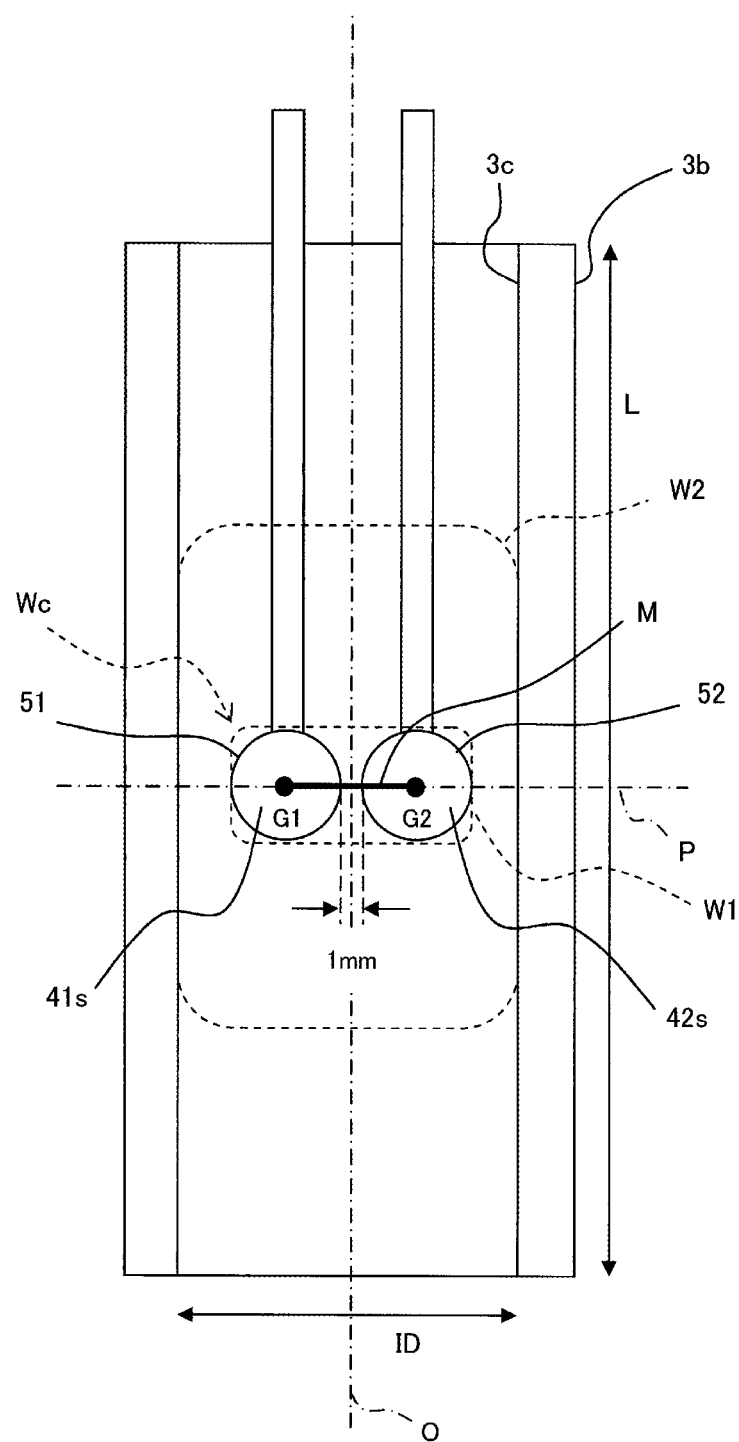
FIG. 5 is a diagram explaining how to specify the minimum dimensions for the opening of a heating furnace.

For this reason, as illustrated in FIG. 5, the minimum dimensions of the opening W (opening W1) are specified so as to provide visual access to all of or most of the inside of the container 51 and the container 52 (the container 52 being the same as the container 51, both having an inner diameter of 3 mm) through the opening W1 when viewed in a direction perpendicular to the axial direction O and to the mounting faces 41s and 42s (looking down the top face of the heating furnace 3 in FIG. 1). Here, the centers of gravity G1 and G2 of the mounting faces 41s and 42s of the sample holders 41 and 42 are used as reference because G1 and G2 do not vary with the container shape and the container inner diameter of the sample containers.

Specifically, the opening W1 measures 7 mm or more as measured with respect to the center of a virtual virtual segment M connecting the centers of gravity G1 and G2 in direction P along the virtual segment M, and 3 mm or more as measured with respect to the center of the virtual segment M in a direction (axial direction O) perpendicular to the virtual segment M, and overlies at least the virtual segment M as viewed the direction perpendicular to the axial direction O and to the mounting faces 41s and 42s. Here, measuring 7 mm in direction P along the virtual segment M means that the maximum length of the opening W1 in direction P is 7 mm, and measuring 3 mm in axial direction O means that the maximum length of the opening W1 in axial direction O is 3 mm. Accordingly, the corner portion Wc of the opening W1 does not need to be a right angle, and may be rounded as shown in FIG. 5. It is, however, required that the arc of the corner portion Wc be a ¼ of the circumference of a circle with a radius of 3 mm to conform to at least the inside of the containers 51 and 52.

The length along the virtual segment M in direction P is 7 mm because the sample containers 51 and 52 with the minimum inner diameter of 3 mm cannot be any closer than about 1 mm to each other along direction P without affecting each other by their heat. (It is assumed here that the sample holders 41 and 42 are disc-shaped with a diameter of about 3 mm.) The opening W1 is therefore the smallest when it is an oval occupied by 3 mm-radius circles with the centers lying on the centers of gravity G1 and G2, and the region that remains after removing these circles.

With an opening W that is too large, it may not be possible to sufficiently control the insulation and heating of the samples $S_1$ and $S_2$ in the furnace tube, and the accuracy of thermal analysis may suffer when observing the thermal analysis sample under high temperatures (for example, 500° C. or more).

In order to ensure that the sample is observed in a reliably heated state even under high temperatures, the maximum dimensions of the opening W (opening W2) are preferably such that the length along the axial direction O is ½ or less of the length L of an inner surface 3c of the heating furnace, and that the length along the direction P perpendicular to the axial direction is no greater than the diameter ID of the inner surface 3c of the heating furnace. Apparently, the opening W2 is positioned so as to confine the minimum dimensions of the opening W1.

Changes in the samples $S_1$ and $S_2$ occurring inside the furnace tube 9 during a thermal analysis can be observed through the opening W described above. For example, in the example of FIGS. 1 and 2, imaging device (for example, such as a camera, a digital camera, a video camera, and an optical microscope) 90 is arranged above the opening W for the observation of samples $S_1$ and $S_2$ during a thermal analysis. The samples can be observed while sufficiently insulating and heating the furnace tube and ensuring the accuracy of thermal analysis even in a thermal analysis performed under high temperatures (for example, 500° C. or more).

Figure 6:
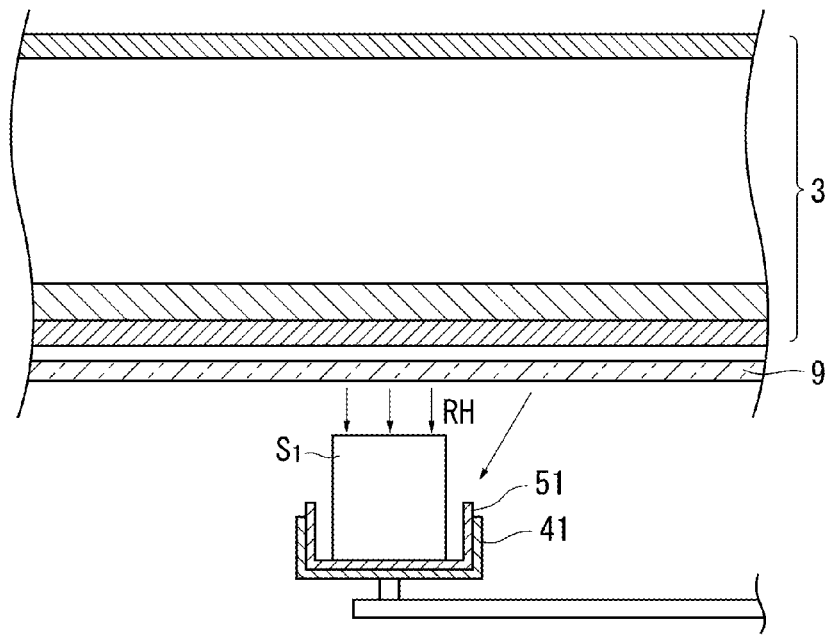
FIG. 6 is a diagram representing the radiation of radiation heat when the heating furnace is not provided with an opening.

The provision of the opening W is advantageous in the following respect. Specifically, as illustrated in FIG. 6, the furnace tube 9 is entirely surrounded by the heating furnace 3, and the sample container 51 for the measurement sample $S_1$ is an open container with the opening facing the heating furnace 3 to measure weight changes in the Thermogravimetry (TG) performed with the furnace tube 9. In this case, the radiation heat RH from the heating furnace 3 is absorbed by the sample container 51 and other components, and directly radiates onto the measurement sample $S_1$ inside the sample container 51.

When performing Thermogravimetry (TG) and Differential Thermal Analysis (DTA) at the same time, DTA obtains a differential heat signal resulting from the melting, decomposition, or other changes of the measurement sample $S_1$. However, the amount of the radiation heat RH absorbed by the measurement sample $S_1$ changes when changes occur in sample color, or when the measurement sample $S_1$ melts and changes its shape under heat. Such changes in radiation heat are reflected in the differential heat signal, and the measurement accuracy suffers.

Figure 7:
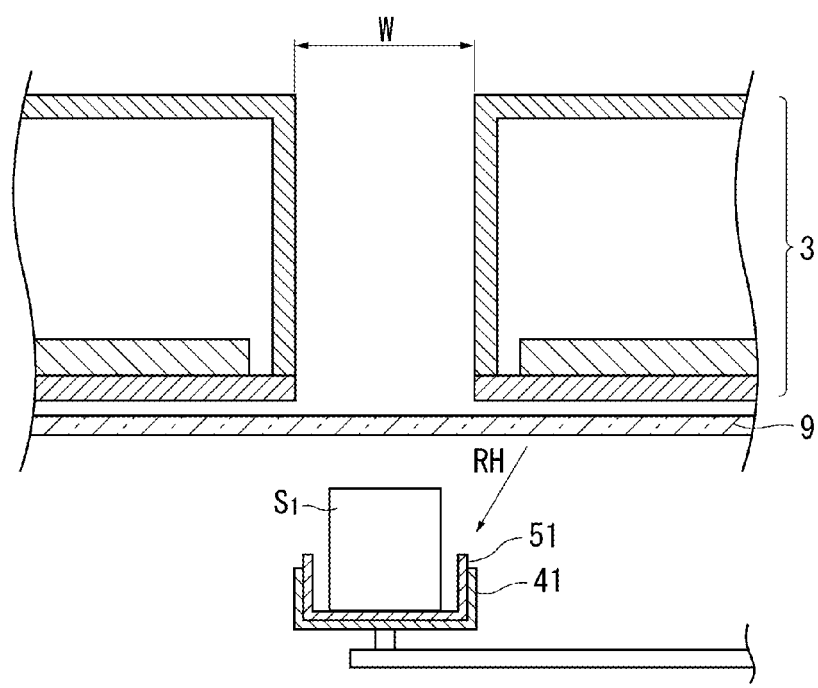
FIG. 7 is a diagram representing the radiation of radiation heat when the heating furnace is provided with an opening.

With the opening W provided in the heating furnace 3 as shown in FIG. 7, the radiation heat RH from the heating furnace 3 does not radiate onto the measurement sample $S_1$ directly below the opening W, and the radiation heat RH that directly radiates onto the measurement sample $S_1$ inside the sample container 51 greatly decreases. The amount of the radiation heat RH absorbed by the measurement samples $S_1$ thus does not vary greatly even when changes occur in the shape or color of the measurement sample $S_1$ by heating, making it possible to suppress lowering of the measurement accuracy of the differential heat signal.

Note that components such as the sample container 51 other than the measurement sample $S_1$ do not change shape or color by being heated, and any absorption of radiation heat RH by these members does not affect the measurement accuracy of the differential heat signal.

Figure 8:
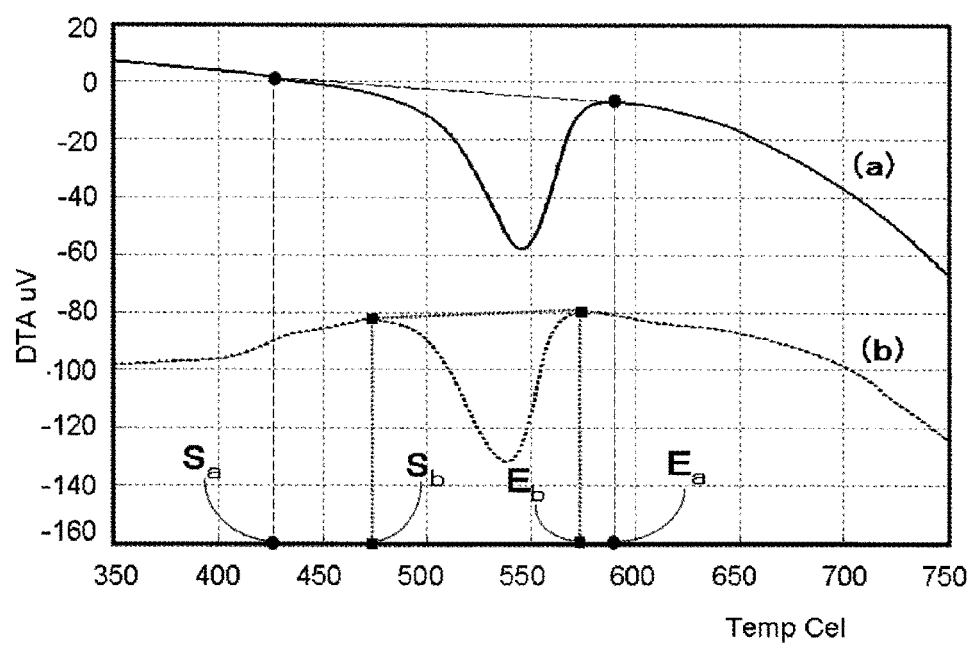
FIG. 8 is a diagram representing the results of Differential Thermal Analyses (DTA) actually performed for calcium oxalate hydrate with and without the opening.
Figure 9:
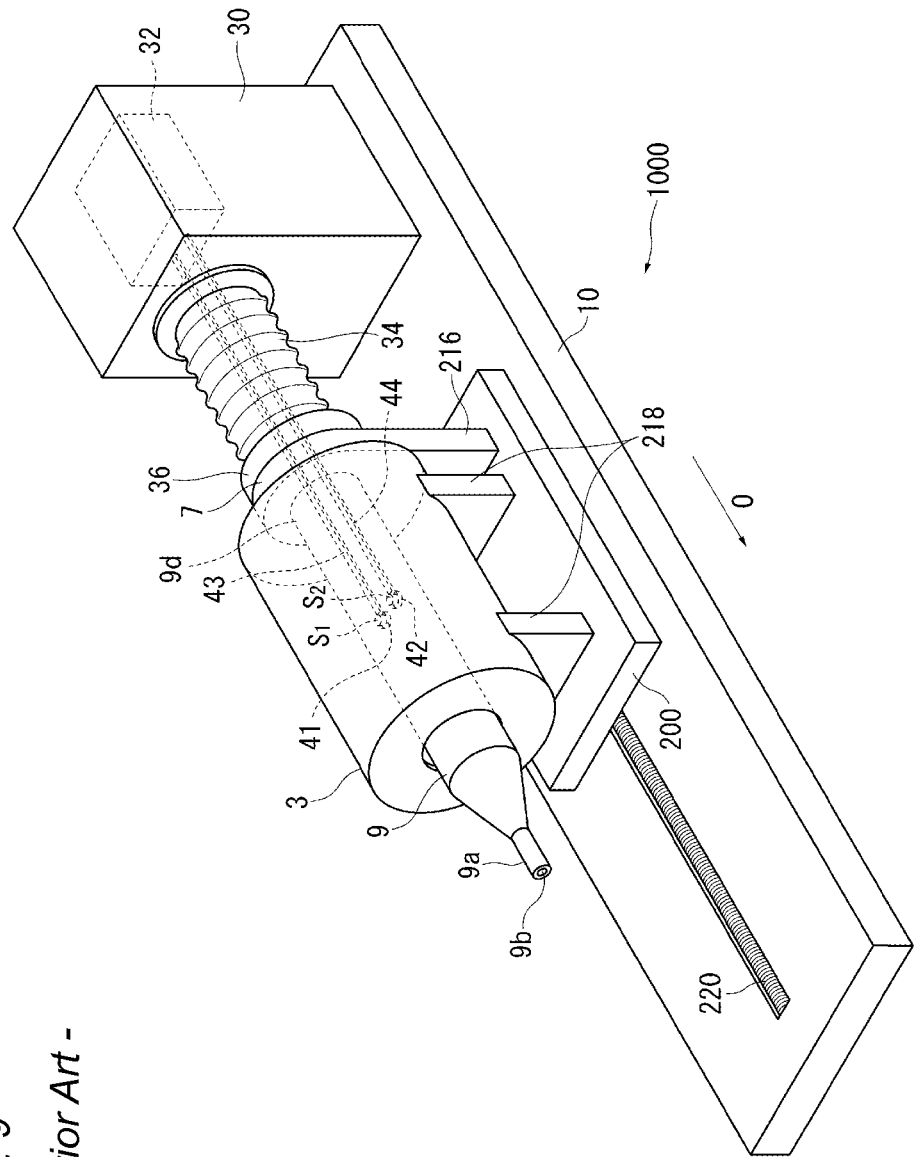
FIG. 9 is a perspective view illustrating a Thermogravimetric (TG) apparatus of related art.
Figure 10:
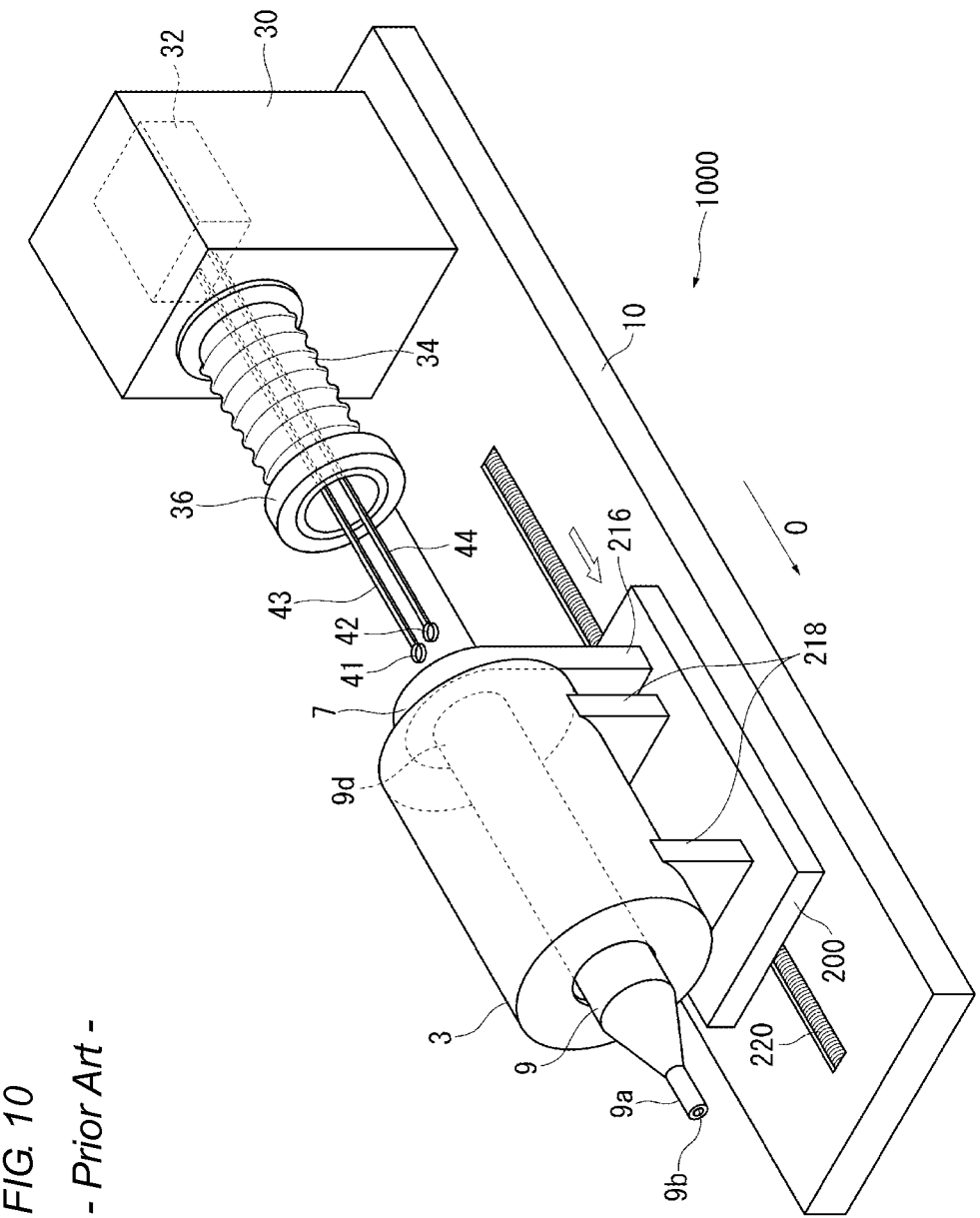
FIG. 10 is a diagram showing how samples are set or replaced in the Thermogravimetric (TG) apparatus of related art.

FIG. 8 represents the results of the Differential Thermal Analyses (DTA) actually performed for calcium oxalate hydrate with and without the opening W. The opening W had the horizontal/vertical dimensions of 10/13 mm, where the vertical represents axial direction O, so as to completely cover the containers 51 and 52 (each having an inner diameter of 5 mm) within the opening W even after the thermal expansion of the balance beams 43 and 44 in axial direction O. An endothermic peak due to the heat decomposition of the dehydrated calcium oxalate occurs in the vicinity of 540° C. With the opening W, the baseline occurring before and after the endothermic peak is flat. This makes it possible to more easily determine the start point (start temperature $S_a$) and the end point (end temperature $E_a$) of the decomposition on the baseline in DTA thermal calculations, and to more accurately determine the differential heat. On the other hand, the flatness of the baseline before and after the peak is insufficient without the opening W (the baseline is unstable). This baseline shape thus presents a false decomposition start point (start temperature $S_b$) and a false decomposition end point (end temperature $E_b$) on the line concerning the peak, different from the actual start temperature $S_a$ and end temperature $E_a$, with the result that the calculation accuracy suffers.

The present invention is not limited to the foregoing embodiment, and encompasses various modifications and equivalents as may be included within the spirit and scope of the present invention.

For example, the furnace tube, the heating furnace configuration, and the arrangements of these and other members are not limited to the foregoing examples. The shape and other variables of the opening are also not limited to the foregoing examples.

For sample observation, the imaging device 90 may be arranged at a position where the measurement sample $S_1$ can be directly observed through the opening W (above the opening W in the example of FIG. 1). Alternatively, a mirror or the like may be arranged at a position where the measurement sample S₁ is directly observable, instead of disposing the imaging device 90 at a position where the measurement sample S₁ is directly observable (above the opening W). This effectively prevents image failure by preventing the imaging device 90 from being directly exposed and damaged by, for example, the heat or the generated gas through the opening W, or by preventing fogging of a lens. The imaging device 90 can be arranged at a predetermined position relative to the opening W by fixing a predetermined attachment (for example, such as a cantilever stay, and a bracket) to the thermal analyzer of the present invention, and attaching the imaging device 90 to the fixing portion (for example, a male screw to be mated with the screw hole for fastening a tripod to a digital camera) provided at the tip of the attachment for fixing the imaging device 90. Alternatively, a mirror or the like may be attached to the predetermined attachment (for example, such as a cantilever stay, and a bracket) fixed to the thermal analyzer of the present invention.

The thermal analyzer of the present invention is applicable not only to the Thermogravimetric (TG) apparatus described above, but to all thermal analyses as specified by JIS K 0129: 2005 "General rules for thermal analysis," and that are intended to measure the physical properties of a measurement target (sample) under the program controlled temperatures. Specific examples include (1) Differential Thermal Analysis (DTA) that detects temperatures (temperature difference), (2) differential scanning calorimetry (DSC) that detects a heat flow difference, and (3) Thermogravimetry (TG) that detects masses (weight change).

What is claimed is:

1. A thermo-gravimetric apparatus comprising:
    a furnace tube made of a transparent material in a cylindrical shape, the furnace tube having an outlet at an anterior end portion thereof in an axial direction that is parallel with a horizontal direction;
    a measurement chamber connected air tight to a posterior end portion of the furnace tube in the axial direction;
    a pair of sample holders arranged inside the furnace tube and each comprising a mounting face on which a pair of sample containers, each containing a measurement sample and a reference sample, are mounted respectively;
    a pair of balance arms that are housed inside the furnace tube and supported at a position inside the measurement chamber, the balance arms having an anterior end connected to the sample holders and a posterior end extending in the horizontal direction toward an inside of the measurement chamber;
    a heating furnace configured to have a cylindrical shape, the heating furnace including:
        a cylindrical outer wall;
        a furnace core tube that has a cylindrical shape and that surrounds the furnace tube from an exterior of the furnace tube, the furnace core tube being disposed within the cylindrical outer wall, the furnace core tube having an axis in a direction along the axial direction, a first surface facing an outer wall of the furnace tube, and a second surface facing away from the furnace tube;
        a heater that is fitted to the second surface of the furnace core tube, wherein the heater is disposed within the cylindrical outer wall; and
        a cylindrical outer cylinder that surrounds the heater and having side walls at both ends; and
    a measurement unit arranged inside the measurement chamber and configured to measure changes in physical properties of the measurement sample and the reference sample,
    wherein the heating furnace comprises an opening through which the measurement sample and the reference sample are observable, the opening penetrating through the cylindrical outer wall and the furnace core tube and being located at a position above the center of a virtual segment which connects centers of gravity of the mounting faces of the sample holders, and
    wherein the heater does not overlap the opening in a radial direction heating furnace.

2. The thermo-gravimetric apparatus according to claim 1, wherein the size of the opening is ½ or smaller than a length of an inner surface of the heating furnace in the direction along the virtual segment and is the same or smaller than a diameter of the inner surface of the heating furnace.

3. The thermo-gravimetric apparatus according to claim 1, wherein the furnace tube is made of a material selected from quartz glass, sapphire glass, and YAG ceramic.

4. The thermo-gravimetric apparatus according to claim 1, further comprising:
    an imaging device arranged at a position where the measurement sample is directly observable through the opening.

5. The thermo-gravimetric apparatus according to claim 1, further comprising:
    an optical system arranged at a position where the measurement sample is directly observable through the opening; and
    an imaging device arranged at a position where the measurement sample is observable via the optical system.

6. The thermo-gravimetric apparatus according to claim 1, wherein the opening is formed to have a size, as viewed in a direction perpendicular to the axial direction and the mounting faces, of 7 mm or more in the direction along the virtual segment and of 3 mm or more in the direction perpendicular to the virtual segment.

7. The thermo-gravimetric apparatus according to claim 1, wherein the heater is disposed closer to the furnace core tube, in the radial direction, than to the cylindrical outer wall.

* * * * *